United States Patent [19]

Yock et al.

[11] Patent Number: 5,596,990
[45] Date of Patent: Jan. 28, 1997

[54] ROTATIONAL CORRELATION OF INTRAVASCULAR ULTRASOUND IMAGE WITH GUIDE CATHETER POSITION

[76] Inventors: Paul Yock, 2200 Redington Rd., Hillsborough, Calif. 94010; Yue-Teh Jang, 43659 Skye Rd., Fremont, Calif. 94539; Stephen M. Salmon, 859 Rattan Ter., Sunnyvale, Calif. 94086

[21] Appl. No.: 470,673

[22] Filed: Jun. 6, 1995

[51] Int. Cl.$^6$ .......................................................... A61B 8/12
[52] U.S. Cl. ................................ 128/662.06; 128/660.03
[58] Field of Search .......................... 128/660.08, 660.09, 128/662.03, 662.05, 662.06, 660.03; 73/625, 626, 628

[56] References Cited

U.S. PATENT DOCUMENTS

| | | |
|---|---|---|
| 4,325,257 | 4/1982 | Kino et al. ................................ 73/626 |
| 4,817,613 | 4/1989 | Jaraczewski et al. . |
| 5,054,492 | 10/1991 | Scribner et al. . |
| 5,163,921 | 11/1992 | Feiring . |
| 5,318,032 | 6/1994 | Lonsbury et al. . |
| 5,485,845 | 1/1996 | Verdonk et al. ................... 128/662.06 |

Primary Examiner—George Manuel
Attorney, Agent, or Firm—Townsend and Townsend and Crew LLP

[57] ABSTRACT

Apparatus and method are described for introducing an imaging catheter to the coronary vasculature. A guiding catheter is introduced so that the distal end of the guiding catheter engages a coronary os. The distal end of the guiding catheter is shaped so that a mark on the distal end is oriented in a predetermined orientation relative to the coronary vasculature. An imaging catheter is then introduced through the guiding catheter and an image of the mark is produced with the imaging catheter while in the guiding catheter. In this manner, the relative orientation of the produced image and the coronary vasculature is known.

22 Claims, 5 Drawing Sheets

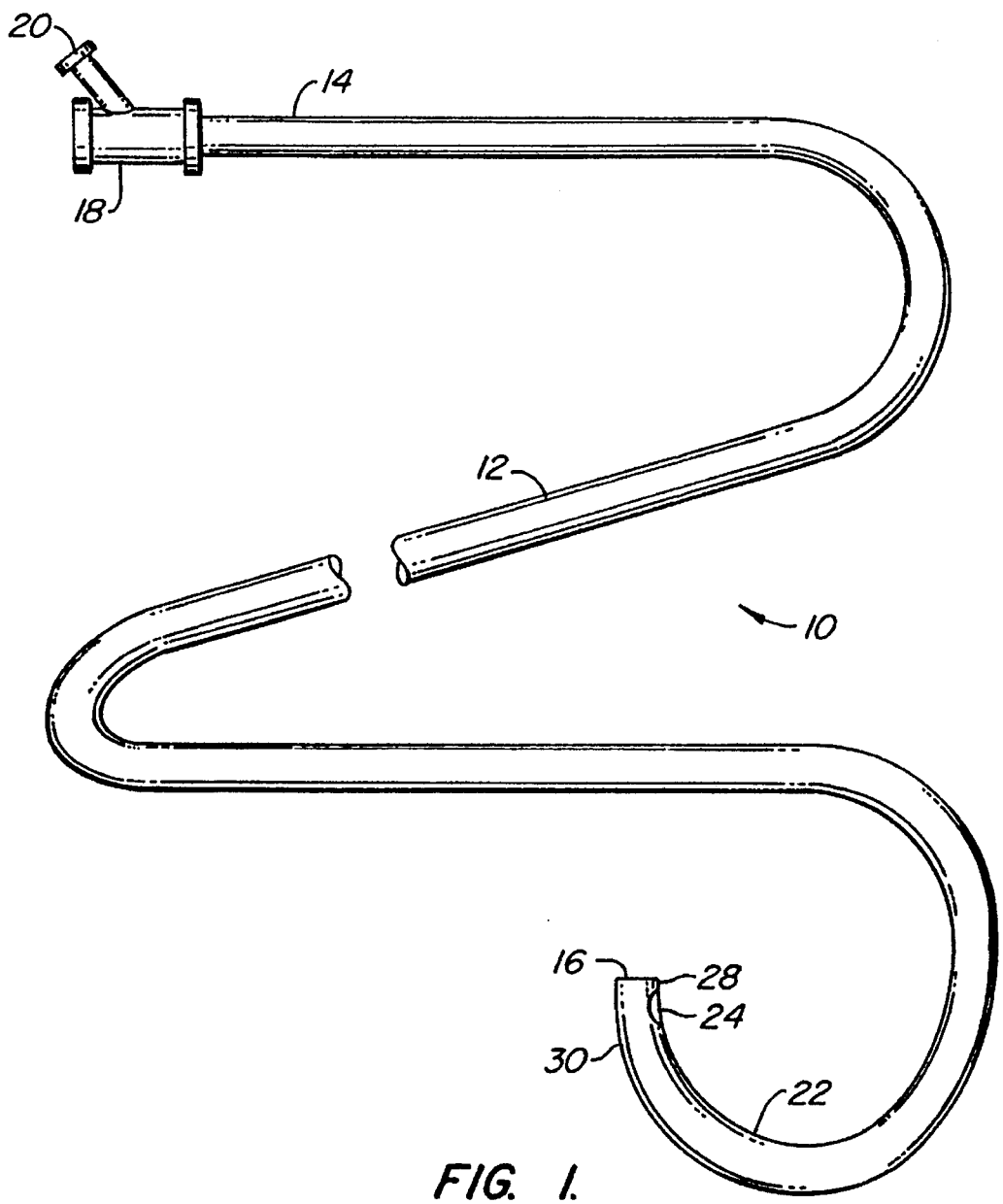
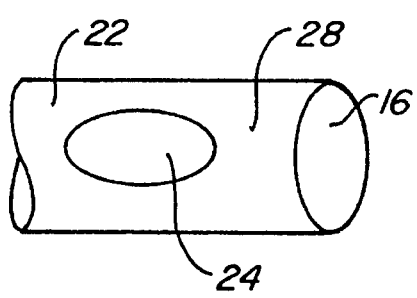
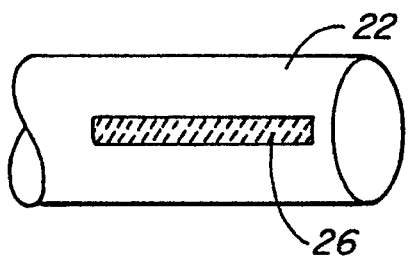
FIG. 1.
FIG. 2.
FIG. 3.

ROTATIONAL CORRELATION OF INTRAVASCULAR ULTRASOUND IMAGE WITH GUIDE CATHETER POSITION

BACKGROUND OF THE INVENTION

1. Field of the Invention

The present invention relates generally to the field of ultrasonic imaging and therapeutic treatment of the vascular anatomy, and particularly for the construction and use of guiding catheters used in accessing the vascular anatomy. More particularly, the invention relates to the rotational correlation of intravascular ultrasonic images produced within such guiding catheters with the vascular orientation of the guiding catheters.

Arteriosclerosis, also known as atherosclerosis, is a common human ailment arising from the deposition of fatty-like substances, referred to as atheroma or plaque, on the walls of blood vessels. Such deposits occur both in peripheral blood vessels that feed the limbs of the body and coronary blood vessels that feed the heart. When deposits accumulate in localized regions of the blood vessels, blood flow is restricted and the person's health is at serious risk.

Numerous approaches for reducing and removing such vascular deposits have been proposed, including balloon angioplasty, where a balloon-tipped catheter is used to dilate a stenosed region within the blood vessel; placement of a stent for maintaining vessel patency after angioplasty; atherectomy, where a blade or other cutting element is used to sever and remove the stenotic material; and laser angioplasty, where laser energy is used to ablate at least a portion of the stenotic material.

In order to more effectively introduce such interventional devices into the vascular anatomy, and particularly into the coronary vasculature, a guiding catheter is generally employed. The guiding catheter is inserted percutaneously into the patient's arterial system, usually by a percutaneous puncture made in the femoral artery in the groin. With the aid of a guidewire (and usually with the assistance of fluoroscopy), the guiding catheter is advanced upwardly through the patient's aorta to the coronary ostia. Usually, the distal end of the guiding catheter is specially shaped to facilitate placement of the distal tip of the guiding catheter against the ostium of one of the coronary arteries and to maintain the guiding catheter in place throughout the procedure. The shape of the distal end allows the distal end of the guiding catheter to point into the ostium, with the catheter body being buttressed against the opposite wall of the aorta.

Once the guiding catheter is in place, therapy proceeds by introducing a therapeutic catheter or other interventional device through the guiding catheter and to the desired treatment location within the coronary arteries. Before employing the therapeutic catheter, however, it is often necessary to properly locate the diseased region of the vessel as well as the position (including the orientation) of the therapeutic catheter relative to the diseased region so that the interventional element on the therapeutic catheter can be employed to treat the diseased region. Directional devices, such as directional atherectomy catheters can be "aimed" at the disease to selectively remove tissue. One approach for visualizing the interior of the vessel is by intravascular ultrasound (IVUS) where a catheter having an ultrasonic imaging element is introduced beyond the guiding catheter and into the vessel to produce cross-sectional images of the vessel. Ultrasonic imaging catheters may also include an interventional element so that therapy can occur without exchanging the imaging catheter for an interventional catheter after imaging has occurred. For example, in the case of atherectomy procedures, one common approach is to employ an imaging catheter having a cutting element located inside of a canoe-shaped housing. On the backside of the housing is a low pressure balloon which is inflated to force the atherosclerotic tissue into the opening of the housing and into the path of the cutter for subsequent removal. Often, the atherosclerotic buildup is only on one side of the vessel wall, commonly referred to as eccentric plaque, thereby making it desirable to position the housing so that the cutting blade is directed only against the eccentric plaque and not the healthy vessel wall. One proposed method for positioning the cutting blade is to rotate the proximal portion of the catheter (which is outside of the patient) until the opening in the housing is aimed at the diseased portion of the vessel. The balloon is then inflated and the cutter is advanced within the housing to shave away the atherosclerotic tissue.

While such ultrasonic images of the vessel assist in locating the existence of the plaque, it has heretofore been difficult to precisely correlate the orientation of the cross-sectional images produced by the imaging catheter with the actual spatial orientation of the image feature within the blood vessel. Many imaging catheter constructions provide no information at all relative to the rotational orientation of the imaging catheter within the blood vessel while the image is being produced. In such cases, correlation of the image with the actual orientation of the blood vessel is difficult or impossible.

It would therefore be desirable to provide improved catheters and methods which would facilitate correlation of an ultrasonic cross-sectional image with the physical orientation of the catheter producing such an image within the coronary vasculature. In this way, regions of the blood vessel requiring therapy can be precisely located and targeted for subsequent interventional treatment. Further, it would be particularly desirable if the rotational orientation of the imaging catheter could be uniquely determined while within the guiding catheter so that the orientation of the imaging catheter can be correlated with the real time ultrasonic image being produced. Most preferably, such improvements should require only modifications of proven catheter designs so that the other functions of the catheters are subsequently undisturbed.

2. Description of the Background Art

A variety of patents describe vascular guiding catheters, including U.S. Pat. Nos. 4,817,613; 5,163,921; and 5,318,032.

U.S. Pat. No. 5,054,492 describes an ultrasonic imaging catheter having both an ultrasonically opaque element and a fluoroscopic marker on the catheter body. Both markers are employed to determine the actual rotational orientation of the catheter within the body lumen being viewed.

SUMMARY OF THE INVENTION

The invention provides a method for introducing an imaging catheter to the coronary vasculature. According to the method, a guiding catheter is introduced so that a distal end of the guiding catheter engages a coronary ostium. The distal end of the guiding catheter is shaped so that a mark on the distal end is oriented in a predetermined orientation relative to the coronary vasculature. An imaging catheter is then introduced through the guiding catheter and is employed to produce an image of the mark while within the guiding catheter. In this way, an image of the mark is produced while the mark is in a known position so that the orientation of the ultrasonic image relative to the actual spatial orientation of the guiding catheter (and to the coronary vasculature) can be correlated.

In one aspect of the method, a screen is employed to produce the image of the mark. The produced image is then rotated until in a preferred orientation relative to the coronary vasculature. Preferably, the orientation of the produced image is aligned with the predetermined orientation of the mark. In this manner, the image displayed on the screen is displayed with the same spatial orientation as both the imaging catheter and the guiding catheter within the coronary vasculature.

In another aspect of the method, the imaging catheter is advanced beyond the guiding catheter and into the coronary vasculature where the imaging catheter is employed to visualize the features of the vessel wall. The actual position of such observed features is then determined based on the orientation of the imaging catheter relative to the coronary vasculature as determined while in the guiding catheter. In this way, a physician can estimate the actual position of the features observed within the vessel based on the produced image while in the guiding catheter. After determining the actual position of the features observed, a diseased region in the coronary vasculature is therapeutically treated.

In an exemplary aspect, the produced image is a cross-sectional image of the mark along with a cross-sectional image of the guiding catheter and the surrounding coronary vasculature. The mark is preferably ultrasonically opaque, and the cross-sectional images of the mark, the guiding catheter, and the coronary vasculature are produced by sweeping an ultrasonic signal in the guiding catheter. In one particular aspect, the mark is a hole in the guiding catheter which appears as a void in the cross-sectional image of the guiding catheter. Alternatively, the mark can be formed as a thin strip of an ultrasonically opaque material on or in the guiding catheter, with the cross-sectional image of the mark appearing as a void or a shadow in the cross-sectional image of the surrounding coronary vasculature.

The invention further provides an improved guiding catheter of the type having an elongate tube with a proximal end, a distal end, a lumen extending between the proximal and distal ends, and a shaped distal tip. Such a guiding catheter is improved by providing an ultrasonically visible mark near the distal end, with the mark being in a unique position relative to the shaped distal tip. In one aspect, the mark is formed as a hole in the catheter body. In another aspect, the mark is an ultrasonically opaque material that is secured on or in the elongate tube, and is preferably formed as a thin strip.

The invention provides a catheter system for treatment of the coronary vasculature. The catheter system includes a guiding catheter having an elongate tube with a proximal end, a distal end, a lumen extending between the proximal and distal ends, and a shaped distal tip. The guiding catheter further includes an ultrasonically visible mark formed near the distal end, with the mark being in a unique position relative to the shaped distal tip. The system further includes an imaging catheter that is translatable through the lumen of the guiding catheter. The imaging catheter includes an imaging element for ultrasonically visualizing the mark and the surrounding coronary vasculature when in the lumen.

In one aspect of the system, a screen is provided and is in electrical communication with the imaging catheter. With the screen, a cross-sectional image of the mark and the surrounding coronary vasculature can be produced. In another aspect, a means are provided for adjusting the orientation of the produced visual image on the screen so that the produced image is in a preferred orientation relative to the coronary vasculature. Preferably, the preferred orientation is aligned with the actual orientation of the distal end of the guiding catheter in the coronary vasculature.

In another aspect of the system, the mark is a hole in the catheter body. Alternatively, the mark includes an ultrasonically opaque material secured on or in the elongate tube.

In still a further aspect, the imaging element includes a rotatable ultrasonic transducer for producing a cross-sectional image of the mark and the surrounding coronary vasculature. Alternatively, a phased array system may be employed to produce the cross-sectional image of the mark and the surrounding coronary vasculature.

BRIEF DESCRIPTION OF THE DRAWINGS

FIG. 1 is a side view of an exemplary guiding catheter according to the present invention.

FIG. 2 is a more detailed view of a distal end of the catheter of FIG. 1 showing a hole formed in the catheter body.

FIG. 3 illustrates an alternative embodiment of the distal end of the catheter of FIG. 1 having a strip of ultrasonically opaque material thereon.

DETAILED DESCRIPTION OF THE SPECIFIC EMBODIMENTS

Figure 4:
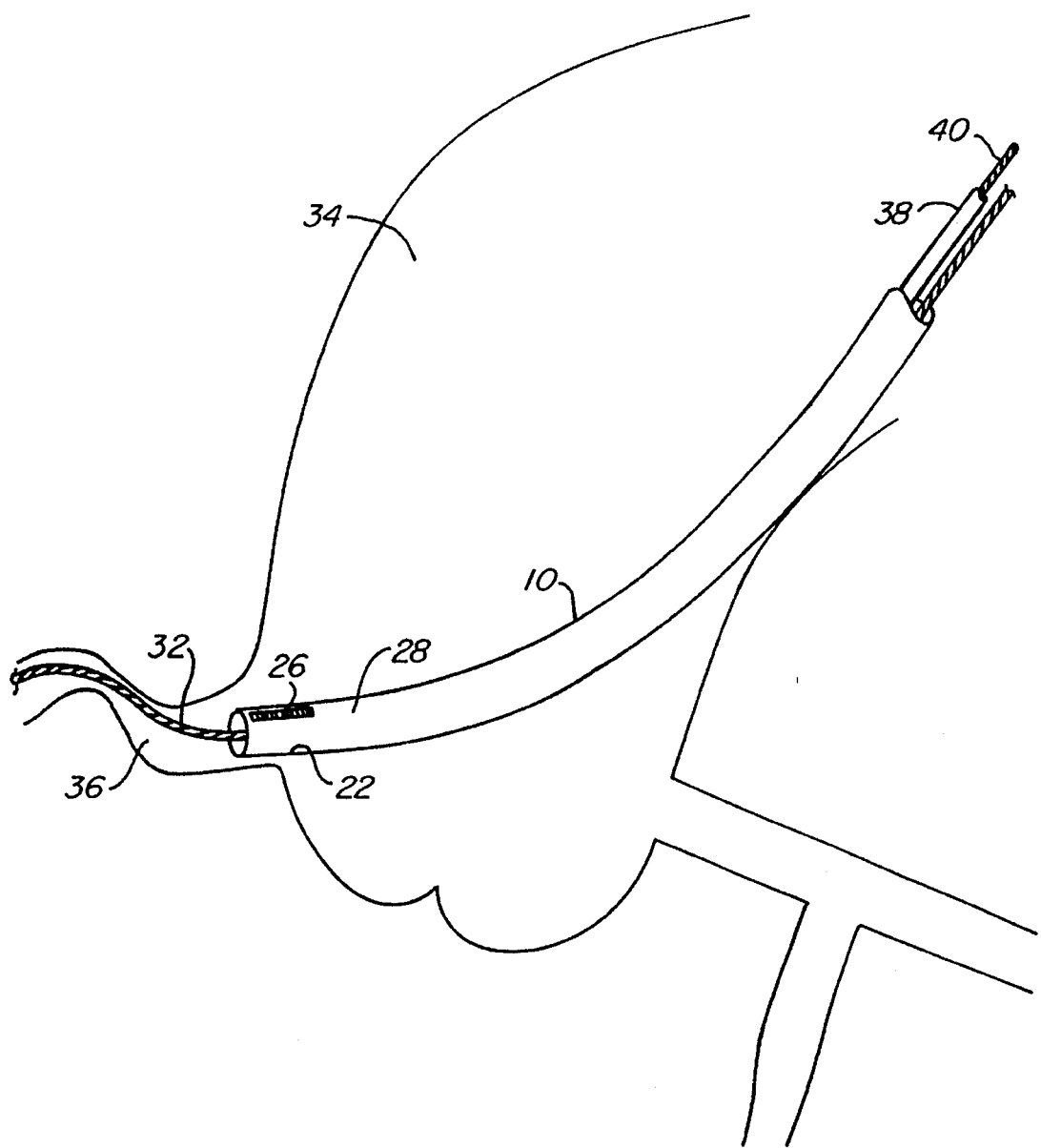
FIG. 4 illustrates placement of the guiding catheter of FIG. 3 with the distal end engaging a coronary ostium according to the present invention.
Figure 5:
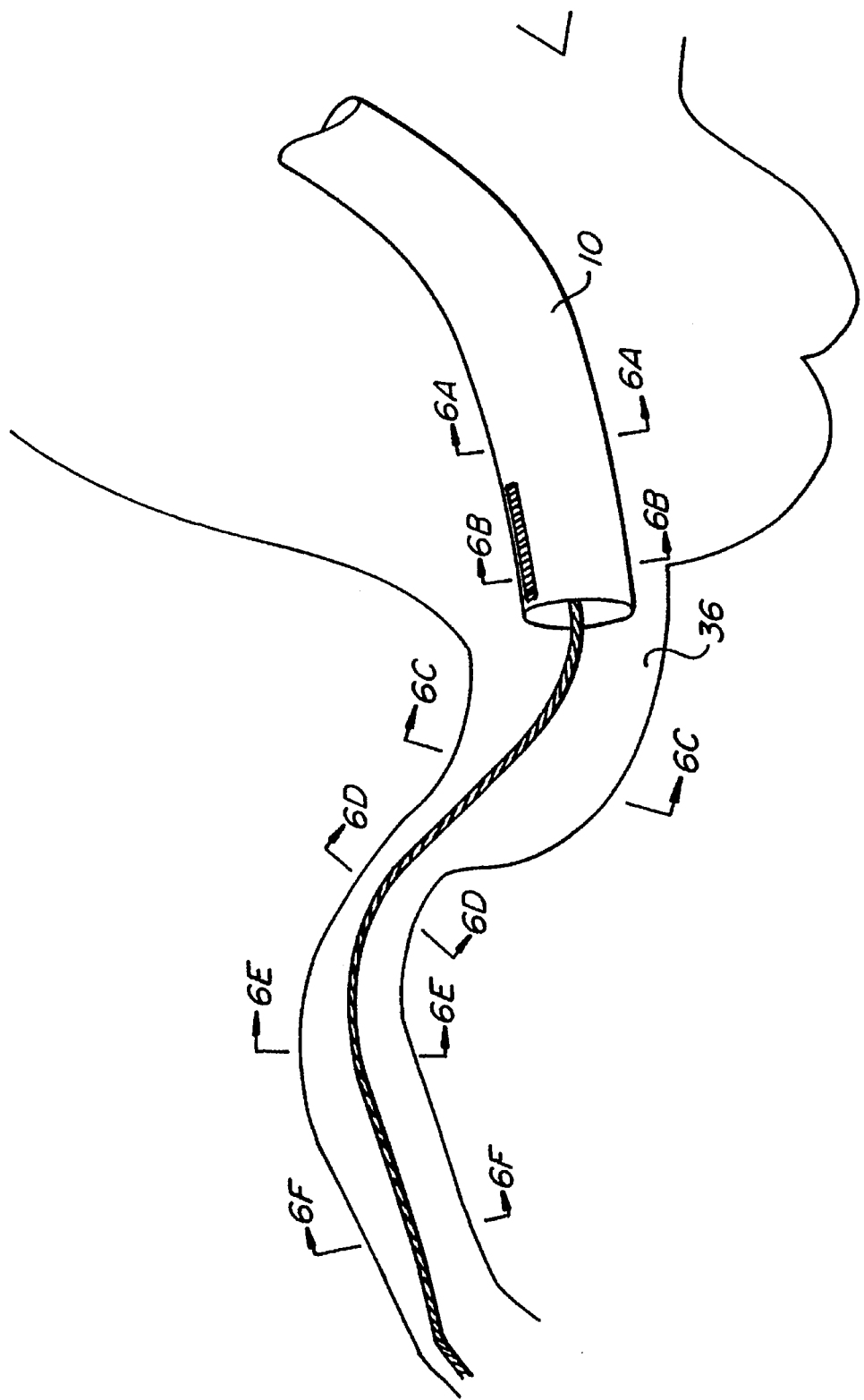
FIG. 5 is an enlarged view of the distal end of guiding catheter of FIG. 3 within the coronary ostium.

Guiding catheters constructed in accordance with the principles of the present invention comprise an elongate tube having a proximal end, a distal end, and a lumen extending therebetween. The guiding catheter further includes a shaped distal tip, such as a bend or a curve in the tube, to facilitate placement of the distal end of the guiding catheter in a coronary ostium. As is known in the art, the distal tip can be shaped to accommodate the particular anatomy of the patient. In this way, the guiding catheter can predictably and repeatedly be orientated in a known position within the coronary ostium. The tip of the guiding catheter includes a superior (pointing up) side and an inferior (pointing down) side. When appropriately positioned, the top of the guiding catheter tip is usually always positioned superior in the ostium of the coronary artery, resulting in the superior side of the guiding catheter being oriented at the top of a fluoroscopic image. In this way, the orientation of the distal end of the guiding catheter is in a known position relative to the patient's vascular anatomy.

The tube of the guiding catheter may be composed of a wide variety of biologically compatible materials, typically being made from natural or synthetic polymers, such as silicone, rubber, natural rubber, polyethylene, polyvinylchloride, polyurethanes, polyesters, polytetrafluoroethylenes (PTFE) and the like. Particular techniques for forming the guiding catheters of the present invention are well known and are described in the patent and medical literature.

The overall dimensions of the guiding catheter will depend on use, with the length of the catheters varying widely, typically between about 50 cm and 150 cm, usually being about 100 cm. The diameter of the tube may also vary widely, with the diameter typically being about 1 mm to 4 mm. Near the distal end of the tube, i.e. usually within about 0 cm to 3 cm of the distal tip, is an ultrasonically visible mark. A wide variety of ultrasonically visible marks can be provided including a hole formed in the tube, an ultrasonically opaque material secured on or in the tube (such as paint, a flat piece of metal ribbon, or other low profile material capable of reflecting acoustic energy), or other ultrasound absorbing material such as urethanes, silicone, epoxies, and the like. The mark is formed near the distal end in a unique position relative to the shaped distal tip. In this manner, when the distal tip is in a known position relative to the vascular anatomy, the orientation of an ultrasonic image produced within the distal tip of the guiding catheter can be determined upon visualization of the mark. Preferred positions for forming the mark include the superior and the inferior sides of the guiding catheter tip. Since the superior side of the guiding catheter tip will usually always be positioned superior in the coronary ostium (and since the orientation of the mark relative to the tip is known) the orientation of any ultrasonic image having the mark can easily be correlated with the orientation of the coronary vasculature. In the event that the ultrasonic image having the mark is not aligned with the fluoroscopic image of the coronary vasculature, the image of the mark can simply be rotated to align the image of the mark with the fluoroscopic image of the coronary vasculature.

To produce the image of the ultrasonically visible mark, an ultrasonic imaging catheter is employed. Such ultrasonic imaging catheters are well known in the art and usually employ an ultrasonic transducer mounted within a distal end of the catheter body and arrange to admit and receive ultrasonic energy within an imaging plane disposed normal to the axial direction of the catheter. Exemplary methods of intravascular ultrasound are described in U.S. Pat. Nos. 4,794,931 and 5,000,185, the disclosures of which are herein incorporated by reference. Such methods include the mechanical rotation of the ultrasonic image transducer about the imaging plane to produce a cross-sectional image of the imaging site.

Before the therapeutic element is employed to treat a diseased region, the imaging element must be properly positioned at the treatment site. Positioning of the therapeutic element is accomplished by determining the orientation of the imaging catheter relative to the vascular anatomy while within the guiding catheter as previously described. The imaging catheter is then distally advanced beyond the distal tip of the guiding catheter and toward the diseased region. As the imaging catheter is advanced through the vessel, images are taken to locate the diseased region. The orientation of the resulting images are estimated based on the orientation of the imaging catheter obtained while within the guiding catheter.

The images produced by the imaging catheter are cross-sectional images of the vascular anatomy. The images are preferably displayed on a monitor screen so that a physician can view the vascular anatomy while performing the procedure. When produced within the guiding catheter, the resulting images include cross-sectional views of the imaging catheter in addition to the vessel wall. When the marker at the distal tip of the guiding catheter comprises a hole in the catheter body, an ultrasonic image of the mark will appear as a discontinuity in the image of the catheter body at the position of the marker. In the event that an acoustically reflective strip of material is employed as the mark, a shadow will be produced in the ultrasonic image, where the position of the shadow corresponds to the position of the marker on the distal tip of the catheter body. In this manner, the physician viewing the image on the monitor will be able to correlate the precise rotational orientation of the guiding catheter relative to the features which are revealed in the image. For example, in the case where the marker is formed on the superior side of the catheter body, the resulting image on the screen should have the shadow extending toward the top of the screen to have the resulting image in the same orientation as the guiding catheter within the coronary vasculature. If the resulting image is not positioned in such a manner, the invention provides for the rotation of the image on the screen so that it is aligned with the orientation of the guiding catheter within the coronary vasculature.

Referring now to FIGS. 1 and 2, an exemplary embodiment 10 of a guiding catheter of the present invention will be described. The guiding catheter 10 includes tubular flexible catheter body 12 having a proximal end 14 and a distal end 16. A proximal housing 18 having a hemostasis valve is generally secured to the proximal end 14 of the catheter body 12 and includes a side port 20 for injecting fluids, such as saline and contrast media, into the guiding catheter 10. At the distal end 16 is a shaped distal tip 22. The distal tip 22 is shaped according to the particular features of the patient's vascular anatomy in order to facilitate predictable and repeatable placement of the distal end 16 into a coronary ostium. At the distal tip 22 is a hole 24. As previously described, the hole 24 serves as an ultrasonic reference marker which appears as a discontinuity in the image of the catheter body 12 when viewed from within the guiding catheter 10 by an ultrasonic imaging catheter.

An alternative embodiment of the distal tip 22 is shown in FIG. 3 and includes a thin strip of acoustically reflective material 26 as the ultrasonic reference marker. The strip 26 produces a shadow in the ultrasonic image of the vascular anatomy produced by the imaging catheter.

Referring back to FIG. 1, the marker 24 is shown on a superior side 28 of the catheter body 12. In this way, when the guiding catheter 10 is introduced into the coronary ostium, the hole 24 is located superior in the coronary ostium. Alternatively, the hole 24 (or strip 26) can be formed at other unique positions at the distal tip 22, such as at an inferior side 30 of the catheter body 12. Since the distal tip 22 is fashioned to be received into the coronary ostium at a known and repeatable position, unique positioning of the hole 24 on the distal tip 22 provides for a known position of the hole 24 relative to the coronary vasculature when the distal tip 22 is received in the coronary ostium.

Referring to FIG. 4, exemplary positioning of the guiding catheter 10 (having the strip 26) will be described in greater detail. Initially, a large guidewire (not shown) is introduced into the aorta 34. Usually, fluoroscopic imaging is employed to assist in the positioning of the guidewire. After the guidewire is placed over the aortic arch, the guiding catheter 10 is advanced over the guidewire until the distal tip 22 is beyond the distal tip of the guidewire. As previously described, the shaped distal tip 22 allows the guiding catheter 10 to be received in the coronary ostium 36 at a known position. The physician will torque and advance the guiding catheter 10 until it "pops" into the appropriate coronary ostium 36. As illustrated in FIG. 4, the strip 26 is on the superior side 28 of the catheter body 12 and is received superior in the coronary ostium 36. In this manner, both the catheter body 12 and the strip 26 are in a known position relative to the coronary vasculature.

Once the guiding catheter 10 is in the desired position, a coronary guidewire 32 is delivered into the coronary artery through the guiding catheter 10. An imaging catheter 38 is then introduced through the guiding catheter 10, typically over the guidewire 32. The imaging catheter 38 includes a cable 40 for rotating the ultrasonic transducer (not shown) in the catheter 38. Alternatively, a phased array catheter system can be employed to image the vessel walls.

Figure 6A:
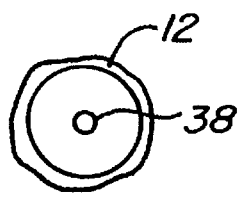
FIGS. 6A–6F illustrate the ultrasonic images which would appear on a monitor screen when an ultrasonic imaging catheter is at each of the rotational orientations illustrated by lines A—A through F—F in FIG. 5.
Figure 6B:
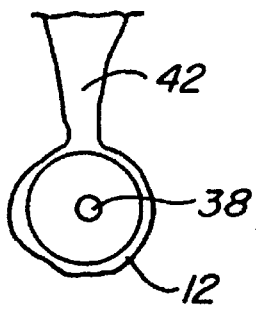

Referring to FIGS. 5 and 6A–6F, ultrasonic imaging of coronary vasculature will be described. FIGS. 6A–6F illustrate monitor images produced by the imaging catheter 38 at lines A—A through F—F of FIG. 5, respectively. As shown in FIG. 6A, the ultrasonic image produced within the guiding catheter 10 reveals the imaging catheter 38 and the guide catheter body 12. The cross-sectional image produced by the imaging catheter 38 when intersecting the strip 26 is shown in FIG. 6B. The resulting image reveals the imaging catheter 38 and the catheter body 12. The image of the strip 26 appears as an acoustic vector 42 extending from the image of the outside catheter wall (much like a lighthouse beacon). As shown in FIG. 6B, the vector 42 extends toward the top of the screen and is therefore aligned with the actual orientation of the strip 26 within the coronary ostium 36. Hence, a physician viewing the screen of FIG. 6B would have a view of the distal tip 22 in the same spatial orientation as the distal tip 22 held within the coronary ostium 36. Usually, as illustrated in FIG. 7, the vector 42 is not aligned with the actual orientation of the distal tip 22 within the coronary ostium 36. In such an event, the image on the screen can optionally be rotated with a software program until the shadow 42 is aligned with the known position (in this case superior) of the strip 26 and distal tip 22 in the coronary ostium 36.

Figure 6C:
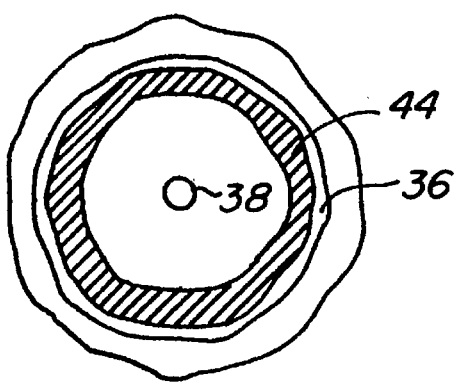
Figure 6D:
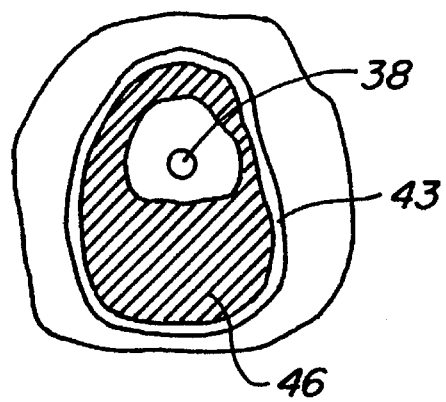
Figure 6E:
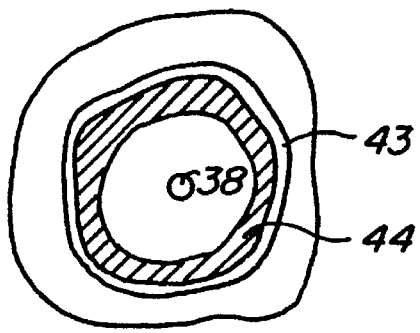
Figure 6F:
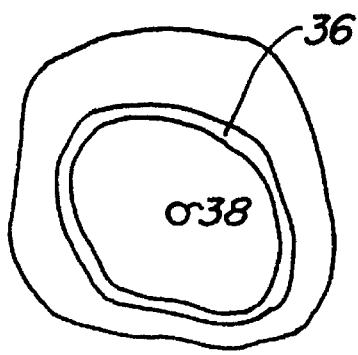
Figure 7:
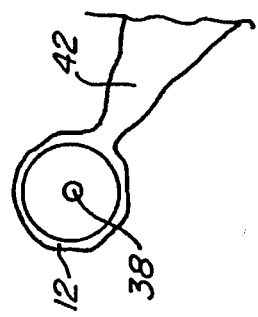
FIG. 7 illustrates the ultrasonic image of FIG. 6B without rotation of the image to a preferred orientation on the screen.

Referring to FIG. 6C, the image produced by the imaging catheter 38 when advanced distally beyond the distal end 16 of the catheter body 12 is shown. The image includes an image of the imaging catheter 38, the annular vessel wall 43 of the proximal coronary artery, which typically appears in three layer structure, and an annular ring of plaque 44 built up on the interior walls of the proximal coronary artery. At position D—D, an amount of eccentric plaque 46 exists in the coronary artery as shown in FIG. 6D. The eccentric plaque 46 is located inferior in the coronary artery, opposite the position of the strip 26 in the coronary ostium 36. Although the image of the strip 26 does not appear on the image of FIG. 6D, the image of the strip 36 obtained while in the guiding catheter 10 is used to estimate the position of the eccentric plaque 46 within the coronary artery since the imaging catheter 38 is advanced just distal, usually only 1 mm to 30 mm from the strip 26. When axially advanced by such an amount, the distal tip 22 experiences little or no rotation within the coronary artery, thereby insuring that the image produced at position D—D is at substantially the same rotational position as the image attained at position B—B. The length of the eccentric plaque 46 is determined by producing images along the coronary artery until the plaque 44 once again becomes annularly disposed about the coronary artery as shown in FIG. 6E, or totally disappears as shown in FIG. 6F.

Figure 8A:
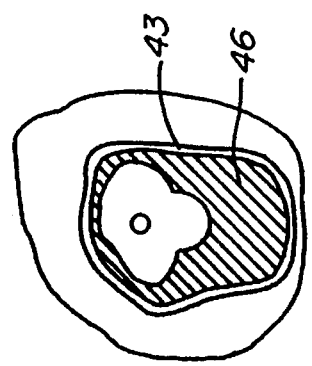
FIG. 8A illustrates the ultrasonic image which would appear on a monitor screen at line A—A of FIG. 8 after the stenotic material has been partially removed and after the cutting catheter of FIG. 8 has been withdrawn.
Figure 8:
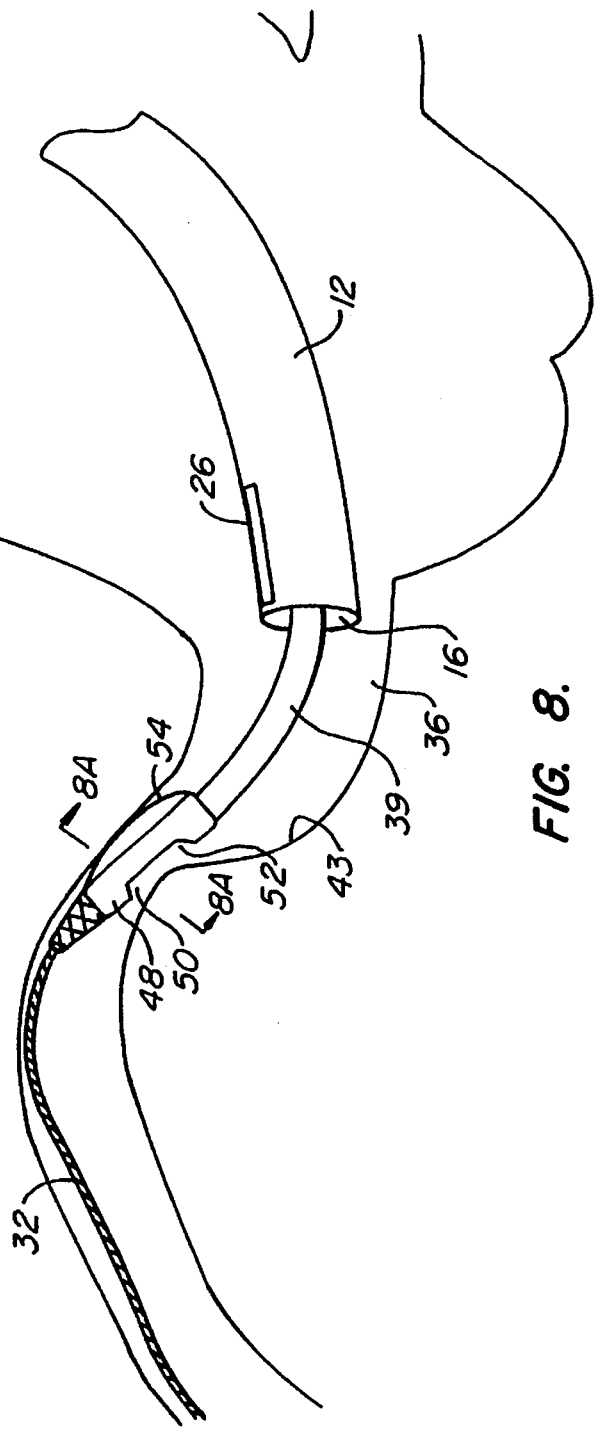
FIG. 8 illustrates a method for therapeutically treating a stenotic region in the coronary vasculature employing a catheter having a cutting element that is introduced through the guiding catheter of FIG. 3.

Referring to FIG. 8, therapeutic treatment of the coronary artery will be described. After producing the image of FIG. 6B so that the relative orientation of the imaging catheter 38 can be determined (and after aligning the vector 42 with the actual orientation of the strip 26 within the coronary ostium 36 if desired or needed), the imaging catheter 38 is distally advanced beyond the distal end 16 of the catheter body 12 to visualize the coronary artery. The imaging catheter 38 is advanced through the coronary artery until reaching the plaque 46 as shown in FIG. 6D. As the imaging catheter 38 is distally advanced toward the plaque 46, the rotational orientation of the imaging catheter 38 will usually remain virtually unchanged. Hence, the position of the imaging catheter 39 relative to the plaque 46 will be known. Based on the image of the plaque 46 and the image produced as FIG. 6B, the actual orientation of the plaque 46 in the artery can be determined. Once the actual orientation of the plaque is known, the imaging catheter 38 is withdrawn from the coronary artery and an atherectomy catheter 39 is introduced over the guidewire.

The atherectomy catheter 39 includes a canoe-shaped housing 48 having an aperture 50 therein. Within the aperture 50 is a cutting element 52 which is employed to shave the plaque 46 from the walls of the coronary artery. A balloon 54 is provided on the housing 48 opposite the aperture 50 for forcing the cutting element 52 against the plaque 46 when inflated. When the area having the eccentric plaque 46 is reached under fluoroscopic guidance, the position of the cutter 52 on the atherectomy catheter 39 can be manipulated to ensure that it is facing the eccentric plaque 46, based on the known orientation of the plaque from the previous ultrasound image. If the cutting element 52 is not adjacent the plaque 46, the atherectomy catheter 39 can be rotated from its proximal end (which is outside the patient) to adjust the rotational position of the cutting element 52. When at the proper location, the balloon 54 is inflated and the cutting element 52 is actuated to remove the plaque 46 from the coronary artery. After removal of the plaque 46, imaging of the area can again occur (as illustrated in FIG. 8A) to determine if sufficient plaque 46 has been removed.

Although described in the context of the right coronary artery, the invention can be used to image and therapeutic treat other areas of the vascular anatomy, such as the left coronary artery or other vessels. The methods of the present invention are particularly useful in the right coronary artery because no branches or other land marks exist in the right coronary ostium to assist in the correlation of the ultrasonic image to the angiographic image.

Although the foregoing invention has been described in some detail by way of illustration and example, for purposes of clarity of understanding, it will be obvious that certain changes and modifications may be practiced within the scope of the appended claims.

What is claimed is:

1. A method for introducing an imaging catheter to coronary vasculature, said method comprising:

introducing a guiding catheter so that a distal end of the guiding catheter engages a coronary ostium, wherein said distal end is shaped so that a mark on the distal end is disposed in predetermined orientation relative the coronary vasculature;

introducing an imaging catheter through the guiding catheter;

producing with the imaging catheter an image of the mark while in the guiding catheter, whereby the relative orientation of the produced image and the coronary vasculature is known.

2. A method as in claim 1, further comprising rotating the produced image on a screen so that the produced image is in a preferred orientation relative to the coronary vasculature.

3. A method as in claim 2, wherein the preferred orientation of the produced image is aligned with the predetermined orientation of the mark.

4. A method as in claim 1, further comprising advancing the imaging catheter into the coronary vasculature, whereby the actual position of features observed can be determined based on the relative orientation of the imaging catheter and the coronary vasculature.

5. A method as in claim 4, further comprising therapeutically treating a diseased region in the coronary vasculature after advancing the imaging catheter into the coronary vasculature and obtaining the image of the diseased region.

6. A method as in claim 1, wherein the produced image is a cross-sectional image of the mark, and further comprising producing with the imaging catheter a cross-sectional image of the guiding catheter and the surrounding coronary vasculature subsequent to producing the image of the mark.

7. A method as in claim 6, wherein the mark is ultrasonically opaque, and wherein the cross-sectional images of the mark, the guiding catheter, and the coronary vasculature are produced by sweeping an ultrasonic signal in the guiding catheter.

8. A method as in claim 7, wherein the sweeping step comprises mechanically rotating an ultrasonic transducer in the guiding catheter.

9. A method as in claim 7, wherein the sweeping step comprises providing the ultrasonic signal with a phased-array catheter system.

10. A method as in claim 7, wherein the mark is a hole in the guiding catheter, and wherein the cross-sectional image of the mark appears as a void in the cross-sectional image of the guiding catheter.

11. A method as in claim 7, wherein the mark is formed as a thin strip on or in the guiding catheter, and wherein the cross-sectional image of the mark appears as a void in the cross-sectional image of the surrounding coronary vasculature.

12. An improved guiding catheter of the type comprising an elongate tube having a proximal end, a distal end, a lumen extending between said proximal and distal ends, and a shaped distal tip, wherein said improvement comprises an ultrasonically visible mark formed near the distal end, wherein said mark is in a unique position relative to the shaped distal tip, and wherein said distal end is open such than an imaging catheter used to visualize the mark may be translated through the lumen, out the distal end, and into a coronary artery to visualize the artery.

13. An improved guiding catheter as in claim 12, wherein the mark comprises an ultrasonically opaque material secured on or in the elongate tube.

14. An improved guiding catheter as in claim 13, wherein the ultrasonically opaque material is formed as a thin strip on or in the tube.

15. An improved guiding catheter as in claim 12, wherein the distal end of the tube is curved.

16. A catheter system for treatment of the coronary vasculature, comprising:

a guiding catheter having an elongate tube with a proximal end, a distal end, a lumen extending between said proximal and distal ends, and a shaped distal tip, wherein the guiding catheter further includes an ultrasonically visible mark formed near the distal end, wherein said mark is in a unique position relative to the shaped distal tip;

an imaging catheter translatable through the lumen of the guiding catheter, the imaging catheter having an imaging element for ultrasonically visualizing the mark and the surrounding coronary vasculature when in the lumen;

a screen in electrical communication with the imaging catheter for producing a visual cross-sectional image of the mark and the surrounding coronary vasculature; and means for adjusting the orientation of the produced visual image on the screen so that the produced image is in a preferred orientation relative to the coronary vasculature.

17. The system of claim 16, wherein the preferred orientation is aligned with the actual orientation of the distal end of the guiding catheter in the coronary vasculature.

18. The system of claim 16, wherein the mark comprises an ultrasonically opaque material secured on or in the elongate tube.

19. The system of claim 16, wherein the imaging element comprises a rotatable ultrasonic transducer for producing a cross-sectional image of the mark and the surrounding coronary vasculature.

20. The system of claim 16, wherein the imaging element comprises a phased array transducer system for producing a cross-sectional image of the mark and the surrounding coronary vasculature.

21. An improved guiding catheter of the type comprising an elongate tube having a proximal end, a distal end, a lumen extending between said proximal and distal ends, and a shaped distal tip, wherein said improvement comprises an ultrasonically visible mark formed near the distal end, wherein said mark is in a unique position relative to the shaped distal tip, and wherein the mark is a hole in the catheter body.

22. A catheter system for treatment of the coronary vasculature, comprising:

a guiding catheter having an elongate tube with a proximal end, a distal end, a lumen extending between said proximal and distal ends, and a shaped distal tip, wherein the guiding catheter further includes an ultrasonically visible mark formed near the distal end, wherein said mark is in a unique position relative to the shaped distal tip, and wherein the mark is a hole in the catheter body; and an imaging catheter translatable through the lumen of the guiding catheter, the imaging catheter having an imaging element for ultrasonically visualizing the mark and the surrounding coronary vasculature when in the lumen.

* * * * *